United States Patent [19]

Idelson

[11] 4,061,654
[45] Dec. 6, 1977

[54] NOVEL TETRAZAPORPHINS

[75] Inventor: Elbert M. Idelson, Newton Lower Falls, Mass.

[73] Assignee: Polaroid Corporation, Cambridge, Mass.

[21] Appl. No.: 358,637

[22] Filed: May 9, 1973

Related U.S. Application Data

[63] Continuation-in-part of Ser. No. 159,492, July 2, 1971, abandoned, which is a continuation of Ser. No. 740,467, June 27, 1968, abandoned.

[51] Int. Cl.² .......................................... C07D 209/00
[52] U.S. Cl. .......................... 260/314.5; 260/250 BC; 260/296 P
[58] Field of Search ........... 260/314.5, 250 BC, 296 P

[56] References Cited

U.S. PATENT DOCUMENTS 2,683,643  7/1954  Baumann et al. ................. 260/314.5
2,701,252  2/1955  Vollmann et al. ................. 260/314.5
2,739,151  3/1956  Rosch et al. ...................... 260/314.5

FOREIGN PATENT DOCUMENTS 702,107  2/1968  Belgium ........................... 260/314.5

OTHER PUBLICATIONS

Moser et al., Phthalocyanine Compounds, pp. 107–108, 274–275 (1963).

Primary Examiner—Richard L. Raymond
Attorney, Agent, or Firm—John P. Morley

[57] ABSTRACT

Ordered tetrazaporphins prepared from the reaction of an aminoiminosubstituted pyrroline with a trihalosubstituted pyrroline in the presence of an acid acceptor and a hydrogen donor.

These compounds are useful as intermediates in the preparation of dyes and pigments, as well as dye developers for photographic processes.

14 Claims, No Drawings

NOVEL TETRAZAPORPHINS

Cross Reference to Related Patent Applications

This application is a continuation-in-part of application Ser. No. 159,492 filed July 2, 1971, now abandoned, which, in turn, is a continuation of application Ser. No. 740,467 filed June 27, 1968 now abandoned.

BACKGROUND OF THE INVENTION

This invention relates to chemical compounds and to methods for the preparation thereof.

One object of the present invention is to provide certain novel chemical compounds as set forth hereinafter which are useful as intermediates in the preparation of dyes, pigments, and dye developers for use in photographic processes.

Another object of the present invention is to provide novel syntheses for preparing such compounds.

Further objects of the invention will in part be obvious and will in part appear hereinafter.

The invention accordingly comprises the processes involving the several steps and the relation and order of one or more of such steps with respect to each of the others and the product possessing the features, properties and the relation of elements which are exemplified in the following detailed disclosure, and the scope of the application of which will be indicated in the claims.

For a fuller understanding of the nature and objects of the invention, reference should be had to the following detailed description.

The tetrazaporphins prepared by the process of this invention may be represented by the formula:

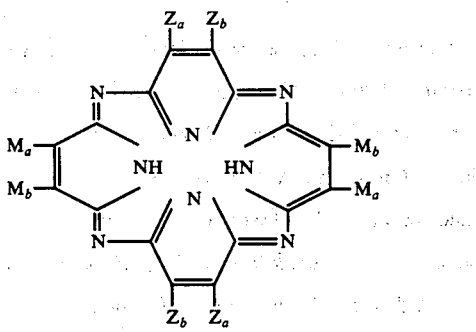

wherein $M_a$, $M_b$, $Z_a$ and $Z_b$ comprise a hydrogen atom, an aliphatic moiety selected from the group consisting of alkyl, alkenyl and alkynl groups of 1 to 6 carbon atoms inclusive, wherein $M_a$ is the same as $M_b$ and $Z_a$ is the same as $Z_b$, and $M_a$ taken together with $M_b$ and $Z_a$ taken together with $Z_b$ can also comprise the atoms necessary to complete ring structures, which ring structures are selected from the group consisting of rings which are unsubstituted, halo substituted, or rings containing one or two alkoxy, and alkyl substituted, wherein the alkyl and alkoxy groups contain from one to six carbon atoms inclusive.

Typical ring structures formed by the junctions of $M_a$ and $M_b$ and $Z_a$ and $Z_b$ include all carbon containing ring systems such as

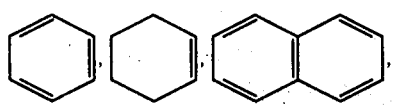

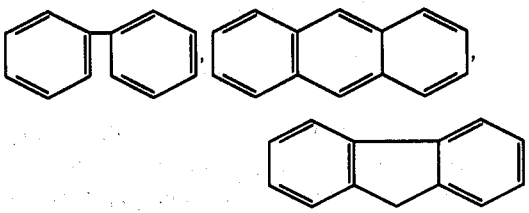

as well as heterosubstituted ring systems such as

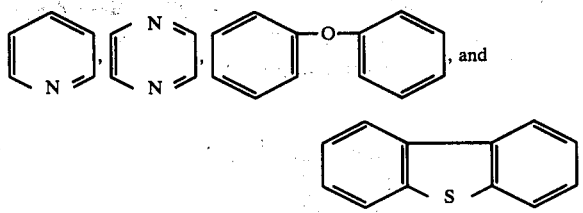

The preferred tetrazaporphins are the phthalocyanines, i.e., those wherein $M_a$ taken with $M_b$ and $Z_a$ taken with $Z_b$ both comprise ring structures designated as $M_c$ and $Z_c$. These compounds are represented by the formula:

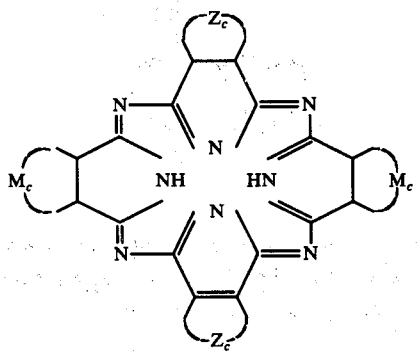

It is seen therefore that the tetrazaporphins of this application wherein M and Z are different have opposing groups which alternate around the ring of the molecule. Henceforth, the discussion will relate to the preferred compounds, the phthalocyanines, however, it is to be understood that the discussion is equally applicable to other tetrazaporphins.

For the sake of ease and convenience, structures as set forth above can also be written as:

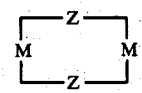

While M and Z have been indicated to be selectable from the same ring structures, such that M and Z can be the same, it will be realized that compounds wherein M and Z are the same have been previously prepared, but not by the method of the present invention. Compounds of the formula:

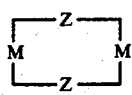

wherein M and Z are different ring structures have never been previously prepared and isolated.

It is felt that a discussion of nomenclature is in order to avoid confusion. Tetrazaporphin compounds can be said to the derived from the geometric repositioning of molecules containing Δ'-pyrroline and pyrrolenine rings. The phthalocyanine compounds in particular, are based on the repositioning of isoindolenine compounds. The basic isoindolenine compound is:

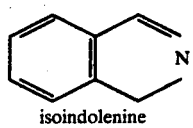
isoindolenine

The 1-amino, 3-imino isoindolenine which contains the ring and pendant nitrogens of 1 quadrant of a phthalocyanine is:

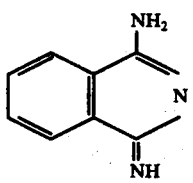

However, phthalocyanines can also be considered as derivatives of phthalimide, which when substituted with imino groups is of the formula:

diiminophthalimide

Some of these derivatives of phthalimide are called phthalimidines.

The generic term aminoiminoisoindolenine shall be used to designate not only the substituted and unsubstituted aminoiminoisoindolenines but also to denote the imidines and any other compounds which comprise a structure fused to a 5 member ring containing 1 nitrogen atom and 4 carbon atoms.

The present invention also utilizes compounds which comprise halogen substituted Δ'-pyrrolines and pyrrolenines. Generically these shall be called trihaloisoindolenines. Here, too, the term is intended to encompass those compounds comprising either ring structures or 2 aliphatic groups joined to the 3 and 4 positions of a 5 member ring of the formula:

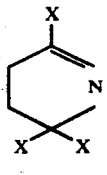

where each X is a halogen

The basic trihaloisoindolenine used in the formation of phthalocyanines by the process of this invention is the compound:

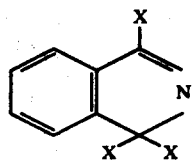
1,3,3-trihaloisoindolenine

At present, there is some disagreement as to the numbering system to be applied to the various atoms of a phthalocyanine compound. As is known, the conventional numbering system avoids the numbering of the fusion points of a fused ring. However, the Russian system — *Nomenclature of Organic Compounds* Moscow, Edition of Academy of Sciences of the U.S.S.R. (1955) — as used in a paper by V.F. Borodkin, Phthalocyanine Analogues, *ZH. Oluschei Khim.*, 1960, 30, 1547–1553, does name the fusion points. Since the Russian system lends itself to easier understanding, it shall be used in this application.

The compound phthalocyanine, wherein M and Z are the same, namely

is of the formula below, and is numbered according to the Russian system as indicated:

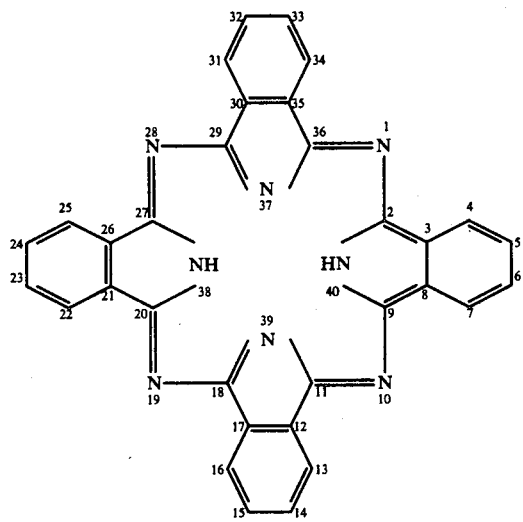

An alkyl group attached to position 5 and 23, for instance, is seen to have no effect on the numbering of the macrocycle itself. However, if M were anthracene instead of benzene as illustrated above, the macrocycle would be renumbered to include the extra ring since it is a part of the macrocycle ring structure per se.

According to the present invention, it has been unexpectedly found that phthalocyanines of the formula:

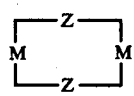

wherein the rings attached to the 3, 8 and 21, 26 points are the same and the rings attached to the 12, 17 and 30, 35 points are the same — [see diagram above], can be prepared as a single pure product. Prior attempts to prepare phthalocyanines of the composition MZMZ gave rise to a mixture of nonseparable products whose average composition was MZMZ. That is, the substituents attached to the 3,8; 12,17; 21,26; and 30,35 positions on the macrocycle would appear in a random order. According to applicant's information and belief, the compound of the structure MZMZ has never been isolated or characterized as such. Typical of such prior art reactions was the one between 5-chlorophthalimide and phthalimide.

Many modes of preparation of phthalocyanines are known in the art. Some of these are described in Moser and Thomas, *Phthalocyanine Compounds* Reinhold, 1963. However, none of these describe the preparation of the pure product of the present invention.

Compounds of the foregoing description are prepared in accordance with the novel process of the present invention by the steps of reacting a compound of the formula:

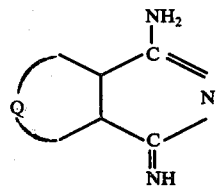

with a compound of the formula:

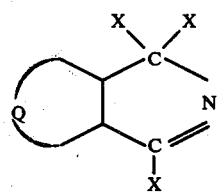

wherein Q represents the atoms to complete either and $M_c$ or a $Z_c$ ring as previously defined and X is a halogen selected from the group consisting of iodine, bromine and chlorine, in the presence of both a hydrogen donor and an acid acceptor.

This process may be more easily understood by reference to the following equation wherein 1,1,3-trichloroisoindolenine is reacted with a substituted 1-amino-3-imino-isoindolenine to prepare a phthalocyanine of the structure:

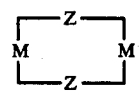

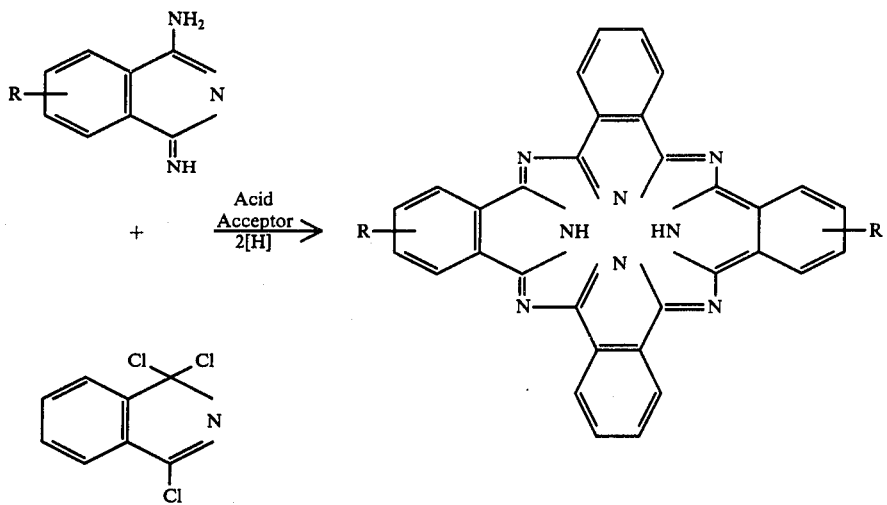

wherein R is an alkyl, alkoxy, halo or haloalkyl substituent.

For ease of understanding, the aninoiminoisoindolenines shall be considered as the M components and the trihaloisoindolenines shall be considered as the A components of the phthalocyanine compound:

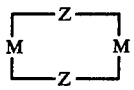

Aminoiminoisoindolenines utilized as starting materials can be prepared in accordance with the process set forth in U.S. Pat. No. 2,752,346 issued to Rösch et al, June 26, 1956. Reference is also made to U.S. Pat. No. 2,701,252 issued Feb. 1, 1955, to Vollmann et al. Trihaloisoindolenines can be prepared according to the process set forth in U.S. Pat. No. 2,701,252 described above.

Suitable modifications within the skill of the art can be carried out to obtain the desired ring system attached to the respective 5 member rings of the M and Z components.

In detail the process entails the condensation reaction between two molecules of the aminoiminoisoindolenine and two molecules of the trihaloisoindolenine to form a phthalocyanine ring of the formula:

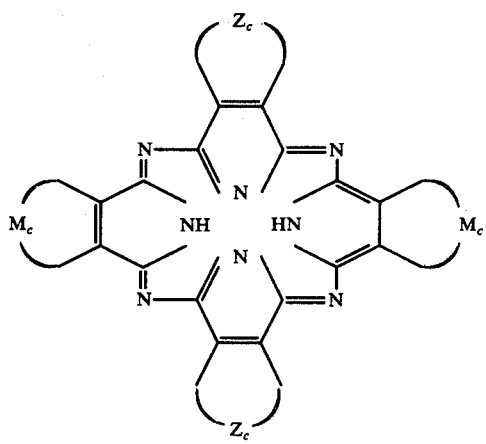

where $M_c$ and $Z_c$ are as previously defined.

It will be recalled that the terms aminoiminoisoindolenine and trihaloisoindolenine are used generically to encompass compounds of the formulae:

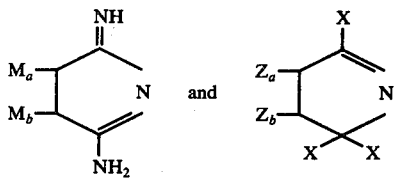

where $M_a$, $M_b$, $Z_a$, $Z_b$, and X are as previously defined. As such it is seen that the process is applicable to the preparation of tetrazaporphins broadly. Since a hydrohalic acid is generated, an acid acceptor or neutralizer is required. A hydrogen donor is also added to provide two hydrogen atoms whose presence is stoichiometrically necessary.

It is seen that from the nature of the reacting groups, namely —NH and —NH$_2$ with Cl⁻ and 2Cl⁻, that only one product can form, namely one of the structure

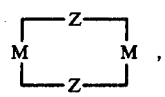

since reaction of two molecules of an M compound with each other or two molecules of a Z compound with each other is not possible, under the above conditions
The

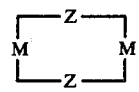

structure can be proven by use of mass spectrometric and x-ray diffraction techniques.

Typical aminoiminoisoindolenines which can be utilized in the process of this invention include:

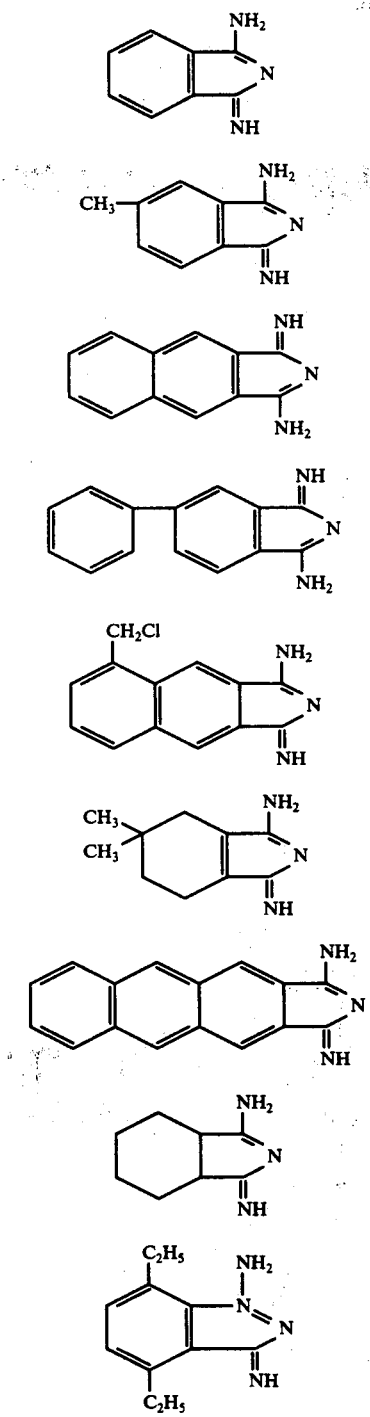

Typical trihaloisoindolenines which can be utilized in the process of this invention include:

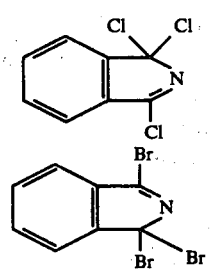

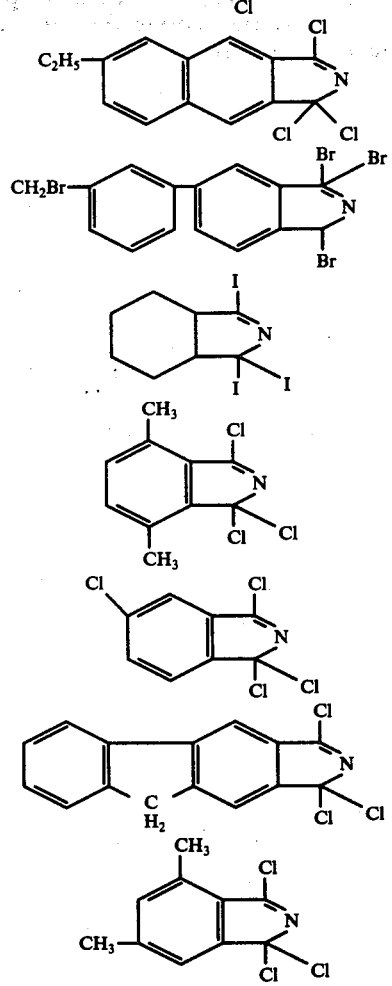

Among the solvents suitable for carrying out this process, mention may be made of dimethylformamide, hexamethylphosphoramide and dimethyl sulfoxide.

As mentioned, a critical feature of the process of the present invention is that the reaction between the aminoiminoisoindolenines and the trihaloisoindolenine must be conducted in the presence of an acid acceptor and a hydrogen donor. Recoverable yields of product have not been obtained unless both these agents are present.

Among the acid acceptors, i.e., neutralizers that can be utilized, mention may be made of sodium bicarbonate, triethylamine and calcium oxide.

Among the suitable reducing agents which are provided to donate hydrogen atoms, mention may be made of the compounds of the hydroquinone series, such as methylphenyl hydroquinone. The preferred compound is hydroquinone itself.

The selection of reaction conditions not specifically described such as time, concentration and pressure, are not critical in the practice of this invention and will be readily apparent to those skilled in the art. Ambient temperature is used for the temperature at which the amininino compound is reacted with trihalocompound.

The selection of solvents, acid acceptors, etc., and procedures to purify the phthalocyanine compounds obtained by the instant process are not critical to the practice of this invention unless so stated and will be apparent to those skilled in the art. The essence of the invention, therefore, is seen to reside in the particular compounds produced and in the process set forth above to obtain such compounds.

As examples of novel compounds within the scope of the formula:

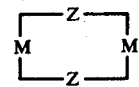

which can be prepared by the above-described process, mention may be made of:

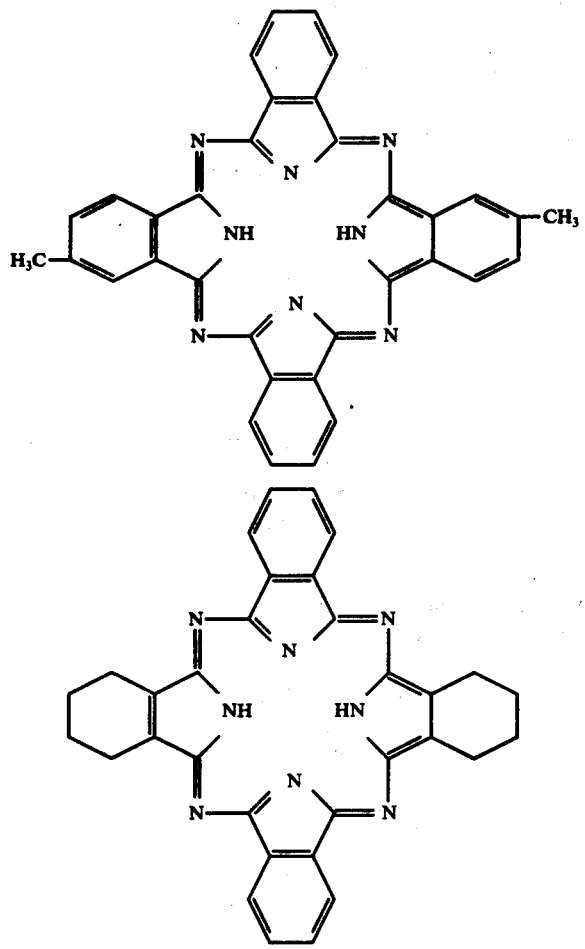

-continued
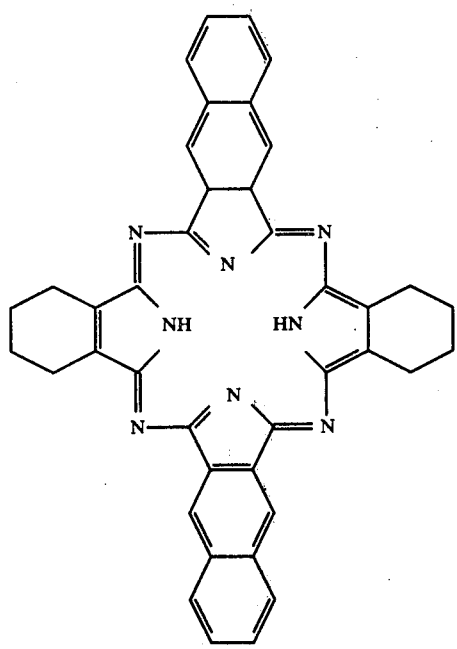
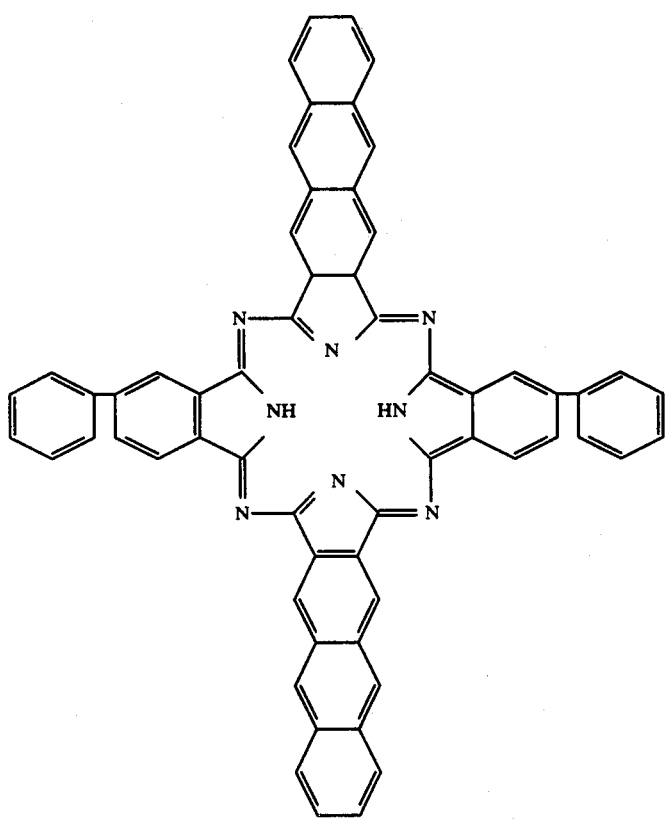

-continued
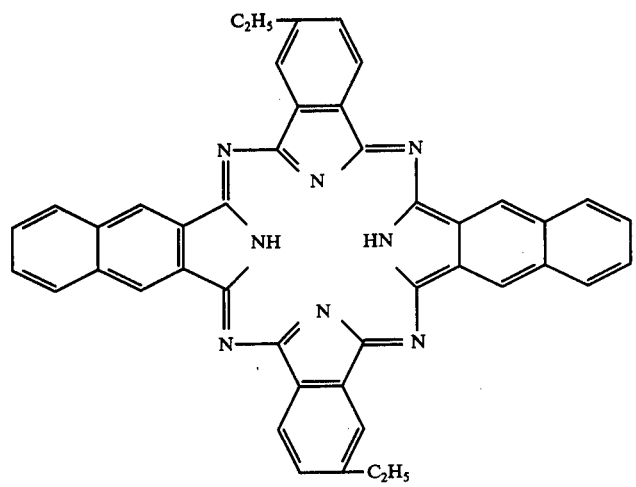
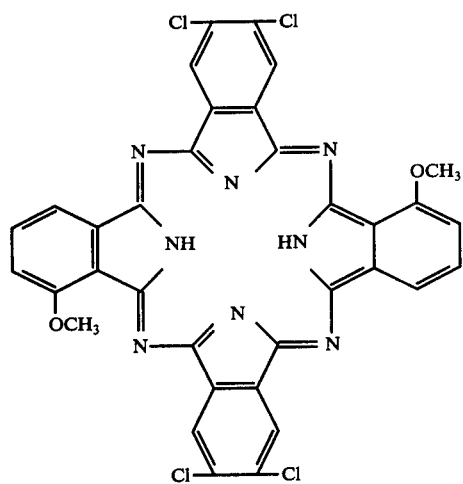
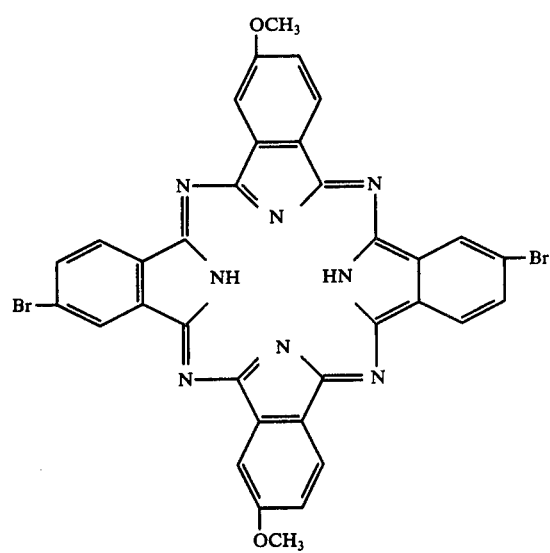

-continued
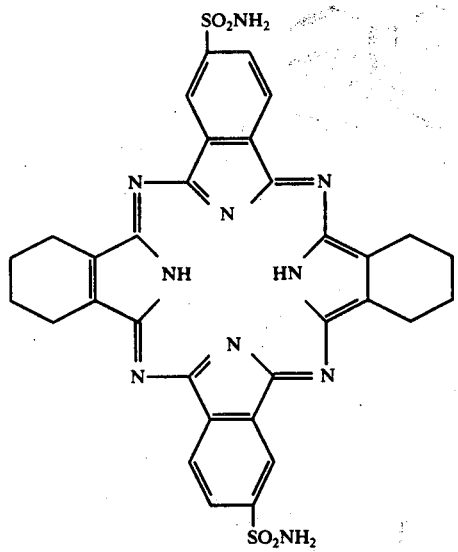
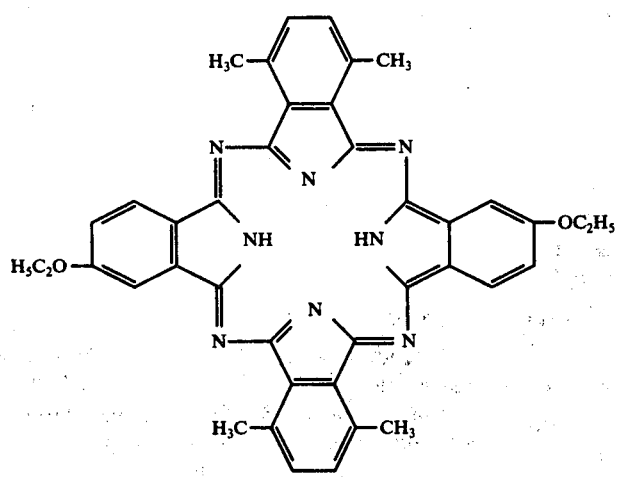
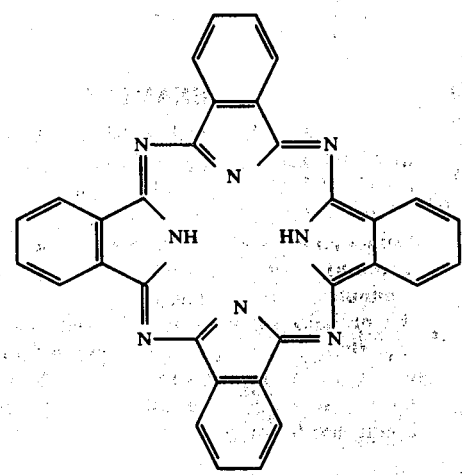

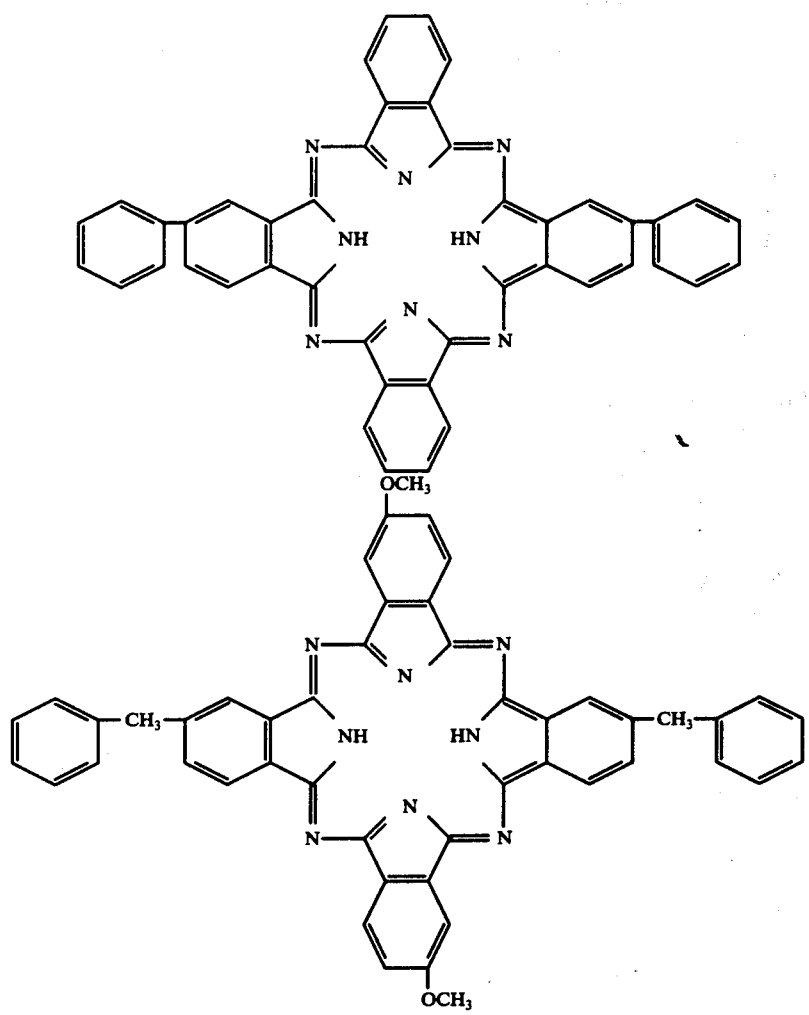

The invention will be illustrated in greater detail in conjunction with the following specific examples which, however, are not to be limited to the details set forth therein and are intended to be illustrative only.

EXAMPLE I 2 g. of 1-amino-3-imino-benzo-(f)-isoindolenine was suspended in 35 ml. of N,N-dimethyl formamide. 0.3 g. of hydroquinone and 2 g. of sodium bicarbonate were added to the mixture. To this was added 2.24 g. of 1,3,3-trichloro isoindolenine whereupon most of this solid dissolved in a yellow solution. After the mixture had been stirred for about 5 minutes, a green solid began to deposit out. After one hour, the phthalocyanine was collected, washed with N,N-dimethyl formamide and acetone and dried. The product was a green-colored solid. The yield was 0.23 g. The product had a molecular weight calculated to be 621.36 and was confirmed by mass spectroscopy.

EXAMPLE II 2.2 g. of 1-amino-3-imino-4-phenyl isoindolenine was suspended in 20 ml. of N,N-dimethyl formamide. 0.55 g. of hydroquinone and 2 ml. of triethyl amine were added to the mixture. To this was added 2.20 g. of 1,3,3-trichloro isoindolenine whereupon most of this solid dissolved in a solution. After the mixture had been stirred for about 5 minutes, a solid began to deposit out. After one hour, the phthalocyanine was collected, washed with N,N-dimethyl formamide and acetone and dried. The product was a dark blue solid. The yield was 0.23 g. The molecular weight was calculated to be 666.0 and was confirmed by mass spectroscopy.

| | Analysis | |
|---|---|---|
| | Found | Calculated |
| C | 79.13 | 79.1 |
| H | 3.93 | 3.91 |
| N | 16.48 | 16.85 |

EXAMPLE III 4.5 g. of cis-hexahydrophthalimidine was suspended in 50 ml. of N,N-dimethylformamide. 1 g. of hydroquinone and 5 g. of sodium bicarbonate were added to the mixture. To this was added 6.5 g. of 1,3,3-trichloro isoindolenine whereupon most of this solid dissolved in a solution. After the mixture had been stirred for about 5 minutes, a solid began to deposit out. After one hour, the phthalocyanine was collected, washed with N,N-dimethylformamide and acetone and dried. The product was a dark blue solid. The yield was 0.23 g. The molecular weight was calculated to be 522.0 and was confirmed by mass spectroscopy.

The preferred compounds have been indicated as comprising substituted and unsubstituted rings containing only carbon atoms. However, the invention also contemplates the use of ring structures containing hetero atoms such as nitrogen, sulfur and oxygen. Typical M or Z structures of such a nature include, but are not limited to:

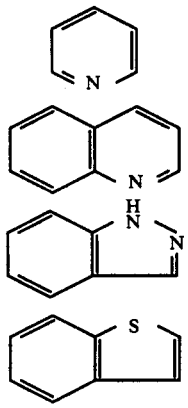

Other phthalocyanine compounds within the scope of this invention include those derived totally or in part from M and Z components of the formulae:

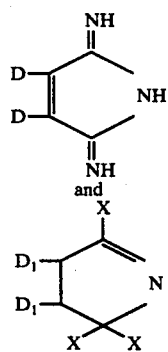

wherein D and $D_1$ are H, alkyl, alkene or alkyne groups, preferably containing 1-6 carbon atoms.

It has been stated that the compounds of this invention are prepared as pure products of a single structure. This is true in all cases in that the structure will be

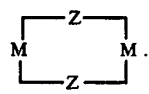

However, it is also to be seen that this one structure can exist as several position isomers, depending on the symmetry of the reactants. If only one isomer of an M component is reacted with but one isomer of a Z component, then the phthalocyanine compound will not exist in alternative isomeric form, in view of the nature of the chemical reactions, in that the Z component's carbon atom bearing two halogen atoms always reacts with the M component's nitrogen atom bearing two replaceable hydrogen atoms, and the monohalosubstituted carbon atom reacts with the nitrogen atom bearing one replaceable nitrogen atoms.

It is to be seen, however, that during the preparation of the two starting reactants, that the unsymmetrical ones are prepared as a mixture of isomers. Reference is made to the Vollman et al patent previously cited to illustrate the process wherein a phthalimide,

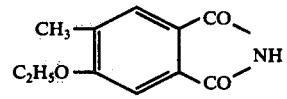

is reacted with a compound such as $PCl_5$ to prepare intermediates

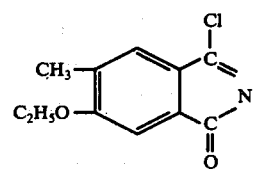

and

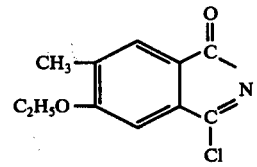

which are then further reacted with additional $PCl_5$ to yield

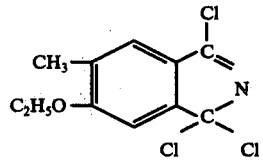

and

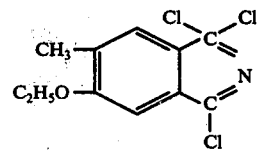

Aminoiminoisoindolenines are prepared in a like manner such that here, too, unsymmetrical compounds will be present in several isomeric forms.

It is readily seen that the number of isomers of the phthalocyanine compound is directly related to the symmetry of its M and Z components from which it is derived.

Thus, if the phthalocyanine compound derived from A—M and B—Z wherein A and B are pendant groups which is

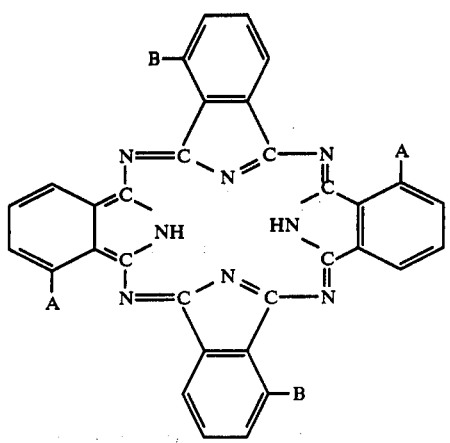

were written geometrically as

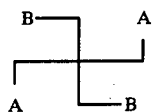

It is readily seen that the compound exists as four possible isomers. They are:

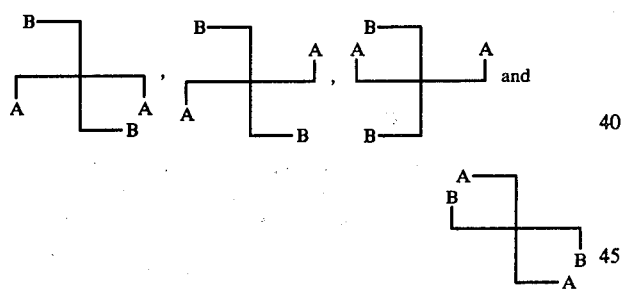

It is fully intended that all of the possible isomeric forms of the compounds set forth by formula within the specification and the appended claims are to be considered within the scope of the invention.

The compounds of the present invention can be utilized as intermediates in the preparation of metallized phthalocyanine compounds such as copper phthalocyanine by boiling the metal-free phthalocyanine with metallic copper in a solvent. Such a process is described in U.S. Pat. No. 2,124,742, issued to Linstead et al, July 26, 1938.

These compounds can be used as intermediates for the preparation of phthalocyanine dyes for textile fibers. Such dye preparations and methods of dyeing are within the skill of the art.

The compounds of the present invention can be further used to prepare phthalocyanine dye developers for the photographic art. The preparation of such dye developers is disclosed in my copending application Ser. No. 694,167, filed Dec. 29, 1967, now U.S. Pat. No. 3,482,972.

Since certain changes may be made in the above products, compositions and processes without departing from the scope of the invention herein involved, it is intended that all matter contained in the above description shall be interpreted as illustrative and not in a limiting sense.

What is claimed is:

1. A phthalocyanine compound of the formula:

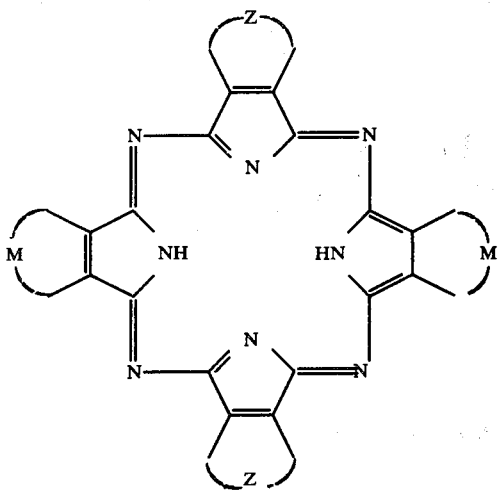

wherein M and Z comprise the atoms necessary to complete carbocyclic rings attached directly to the pyrrolenine ring and wherein M and Z are different ring structures, both being selected from the group consisting of

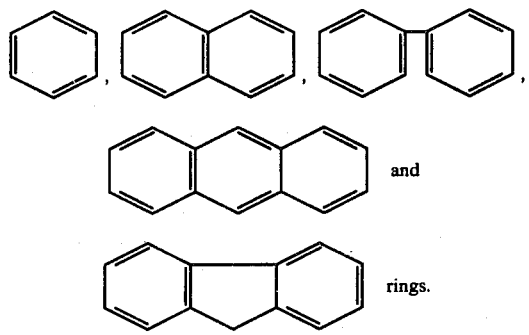

2. The compound

3. The compound

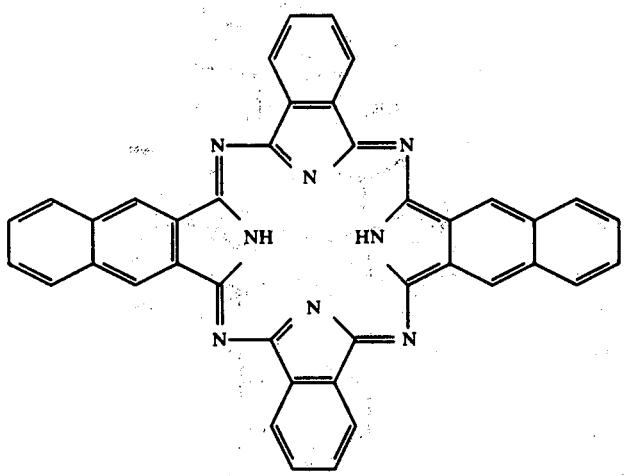

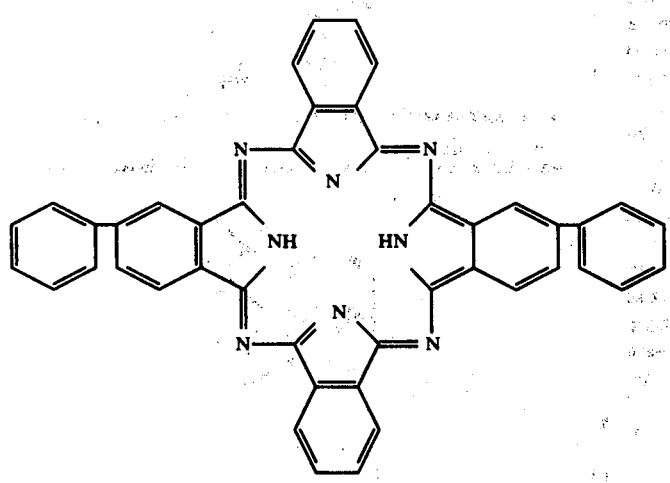

4. A process which comprises reacting a compound of formula:

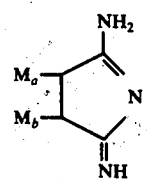

with a compound of the formula:

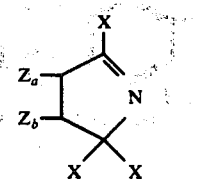

in the presence of an acid acceptor and a hydroquinone compound which can donate hydrogen atoms and wherein $M_a$, $M_b$, $Z_a$, and $Z_b$ comprise a hydrogen atom, an aliphatic moiety selected from the group consisting of alkyl, alkenyl and alkynl groups having no more than 6 carbon atoms inclusive, wherein $M_a$ is the same as $M_b$ and $Z_a$ is the same as $Z_b$, and $M_a$ taken together with $M_b$ and $Z_a$ taken together with $Z_b$ can also comprise the atoms necessary to complete carbocyclic or heterocyclic ring structures attached directly to the pyrrolenine ring which ring structures are selected from the group consisting of unsubstituted, lower alkylsubstituted, lower alkoxysubstituted, and halosubstituted rings, and each X is a halogen atom.

5. A process which comprises reacting an aminoiminoisoindolenine of the formula:

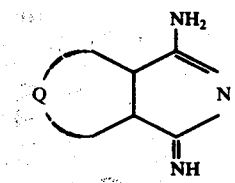

with a trihaloisoindolenine of the formula:

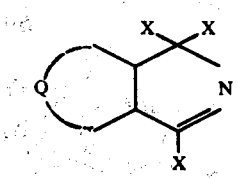

in the presence of an acid acceptor and a hydroquinone compound which can donate hydrogen atoms wherein each X is a halogen atom and each Q comprises the atoms necessary to complete the same or different carbocyclic ring selected from the group consisting of

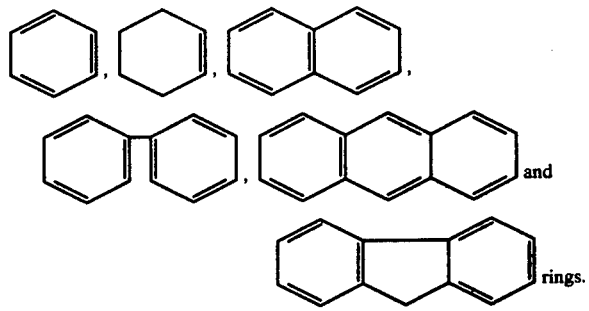

rings.

6. The process of claim 5 wherein the reaction is carried out in a solvent selected from the group consisting of N,N-dimethyl formamide, dimethyl sulfoxide and hexamethylphosphoramide.

7. The process of claim 5 wherein the acid acceptor is selected from the group consisting of triethyl amine, sodium bicarbonate and calcium oxide.

8. The process of claim 5 wherein the aminoiminoisoindolenine is selected from the group consisting of 1-amino-3-imino-benzo-(f)-isoindolenine, 1-amino-3-imino-4-phenyl isoindolenine, cis-hexahydrophthalimidine, and 1-amino-3-amino-isoindolenine.

9. A process which comprises the step of reacting an aminoiminoisoindolenine with a trihaloisoindolenine in the presence of an acid acceptor chosen from the group consisting of triethyl amine, sodium bicarbonate and calcium oxide and a hydroquinone compound which can donate hydrogen atoms and wherein said aminoiminoisoindolenine is chosen from the group consisting of:

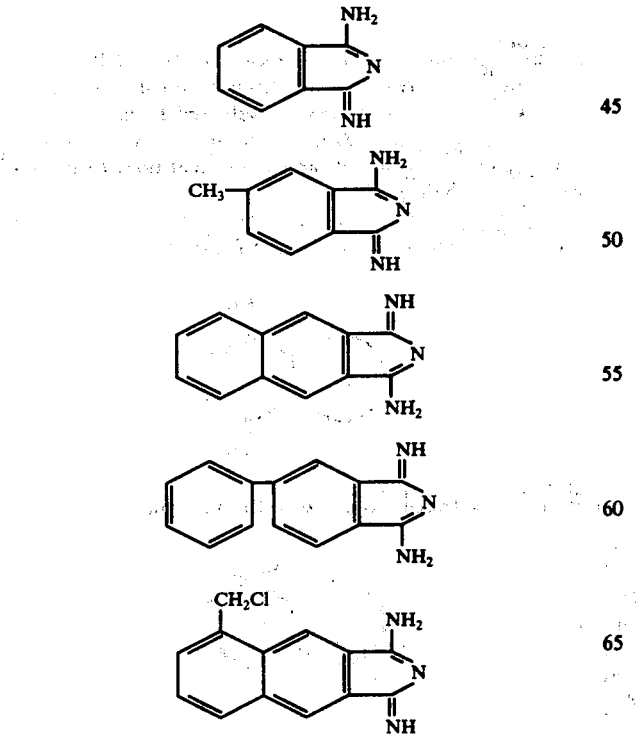

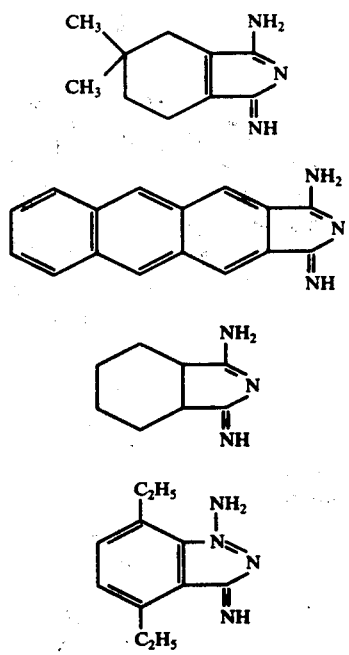

and wherein said trihaloisoindolenine is chosen from the group consisting of:

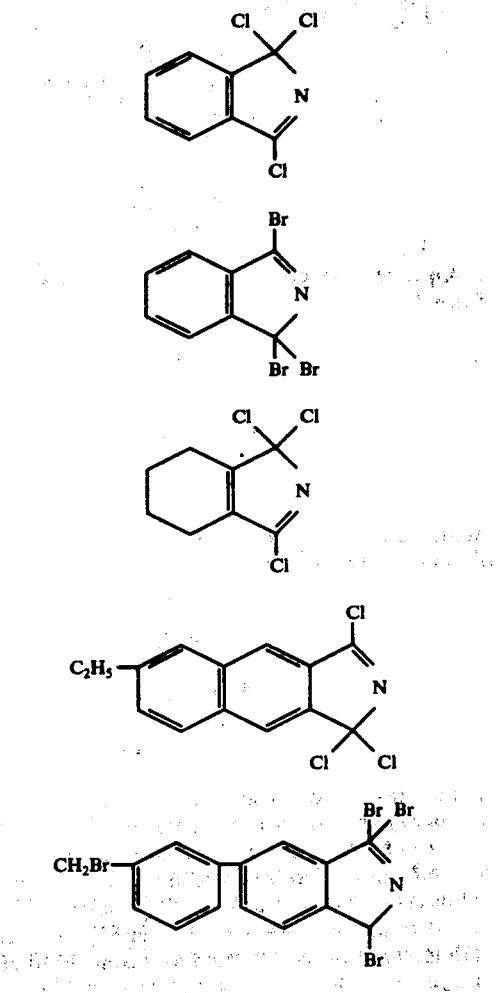

-continued

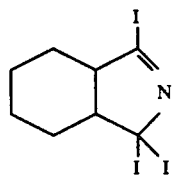
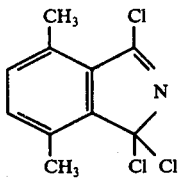
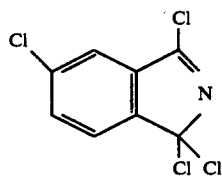
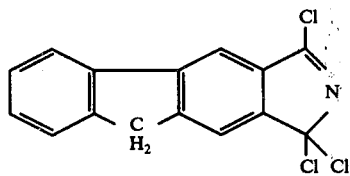

-continued

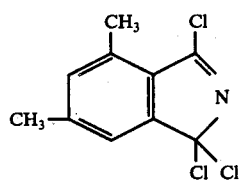

10. The process of claim 9 wherein the reaction is carried out in a solvent selected from the group consisting of N,N-dimethyl formamide, dimethyl sulfoxide and hexamethylphosphoramide.

11. A process which comprises the step of reacting 1-amino-3-imino-benzo-(f)-isoindolenine with 1,3,3 trichloroisoindolenine in the presence of sodium bicarbonate and hydroquinone.

12. A process which comprises the step of reacting 1-amino-3-imino-4-phenyl isoindolenine with 1,3,3 trichloroisoindolenine in the presence of sodium bicarbonate and hydroquinone.

13. A process which comprises the step of reacting 1-amino-3-imino-4-phenyl isoindolenine with 1,3,3 trichloroisoindolenine in the presence of sodium bicarbonate and hydroquinone.

14. A process which comprises the step of reacting 1-amino-3-imino-isoindolenine with 1,3,3 trichloroisoindolenine in the presence of sodium bicarbonate and hydroquinone.

* * * * *